United States Patent
Malchow

(10) Patent No.: US 10,379,040 B2
(45) Date of Patent: Aug. 13, 2019

(54) DETECTING MOISTURE IN SOLAR CELLS

(71) Applicant: Sensors Unlimited, Inc., Princeton, NJ (US)

(72) Inventor: Douglas S. Malchow, Lawrence, NJ (US)

(73) Assignee: Sensors Unlimited, Inc., Princeton, NJ (US)

( * ) Notice: Subject to any disclaimer, the term of this patent is extended or adjusted under 35 U.S.C. 154(b) by 115 days.

(21) Appl. No.: 15/391,065

(22) Filed: Dec. 27, 2016

(65) Prior Publication Data

US 2018/0180538 A1 Jun. 28, 2018

(51) Int. Cl.
*G01N 21/94* (2006.01)
*G01N 33/18* (2006.01)
*G01N 21/3554* (2014.01)

(52) U.S. Cl.
CPC ......... *G01N 21/3554* (2013.01); *G01N 33/18* (2013.01); *G01N 2021/945* (2013.01); *G01N 2201/0686* (2013.01)

(58) Field of Classification Search
None
See application file for complete search history.

(56) References Cited

U.S. PATENT DOCUMENTS

| | | | |
|---|---|---|---|
| 7,355,707 B1* | 4/2008 | Videen | G01N 21/21 356/128 |
| 7,705,978 B2 | 4/2010 | Chou et al. | |
| 8,278,937 B2 | 10/2012 | Vasilyev et al. | |
| 2010/0051905 A1* | 3/2010 | Iguchi | B82Y 20/00 257/14 |
| 2017/0160192 A1* | 6/2017 | Mantyla | G01N 21/3559 |

FOREIGN PATENT DOCUMENTS

| | | |
|---|---|---|
| CN | 205301196 U | 6/2016 |
| JP | 2011023412 A | 2/2011 |
| JP | 2011138969 A | 7/2011 |

\* cited by examiner

*Primary Examiner* — Edwin C Gunberg
(74) *Attorney, Agent, or Firm* — Locke Lord LLP; Scott D. Wofsy; Joshua L. Jones

(57) ABSTRACT

An imaging apparatus includes a camera with a solid-state sensor and an illumination selector. The illumination selector is arranged for optical coupling with the sensor and arranged for communicating electromagnetic radiation within a shortwave infrared narrowband to the sensor. The shortwave infrared narrowband includes a peak absorption or peak reflection wavelength of moisture to infrared illumination to image moisture disposed within a solar cell array.

15 Claims, 4 Drawing Sheets

DETECTING MOISTURE IN SOLAR CELLS

BACKGROUND OF THE INVENTION

1. Field of the Invention

The present disclosure relates to imaging, and more particularly to imaging interiors of sealed structures like solar cell arrays for the presence of moisture.

2. Description of Related Art

Solar cells commonly include photovoltaic materials which generate electrical power in response to illumination by light using the photovoltaic effect. Examples of photovoltaic materials commonly employed in solar cell arrays include mono- and poly-crystalline silicon, amorphous silicon, compound semi-conductors, thin films, and organic-molecule based solar power cells. Structures formed from such photovoltaic materials are typically housed in sealed enclosures which allow incident light to illuminate the photovoltaic material while protecting the photovoltaic structures and associated electrical components from the external environment.

Solar cell arrays are typically long lived. In some solar cells moisture infiltration can infiltrate the enclosure, where it can change the impedance of circuit paths and/or cause electrical shorts or opens to develop in the circuitry. Moisture can also influence the responsiveness of the solar cell photovoltaic material to incident light, such as through optical scattering or by absorption. Further, in cold climates, cyclic freezing and melting can cause mechanical damage to the solar cell, resulting in open circuits or reduced solar sensitivity. It can therefore be necessary to inspect solar cell arrays for the presence of moisture.

Conventional systems and methods for inspection solar cells in production or during installation have generally been considered satisfactory for their intended purpose. However, there remains a need for improved systems and methods for detecting moisture intrusion in solar cells while in the field. The present disclosure provides a solution for this need.

SUMMARY OF THE INVENTION

An imaging apparatus includes a camera with a solid-state sensor and an illumination selector. The illumination selector is arranged for optical coupling with the sensor and arranged for communicating electromagnetic radiation within a shortwave infrared (SWIR) narrowband to the sensor. The SWIR narrowband includes a peak absorption or peak reflection wavelength of moisture to infrared illumination to image moisture disposed within a solar cell array.

In certain embodiments, the sensor can be responsive to illumination within a waveband between about 0.8 microns and about 2.6 microns. The sensor can include an array of indium-gallium-arsenide photodiodes. The selector can include a light source constrained to emit electromagnetic radiation within the SWIR narrowband. The light source can include an incandescent, halogen, light-emitting-diode, or laser illuminator.

In accordance with certain embodiments, the SWIR narrowband can have a bandwidth that is between about 10 nanometers and about 100 nanometers. The SWIR narrowband can include a peak absorption wavelength selected from a group including 0.97, 1.2, 1.44, and 1.92 microns. The SWIR narrowband can include a peak reflection wavelength selected from a group including 1.06, 1.24, 1.66, and 2.22 microns. It is contemplated that the selector can includes filter arranged to communicate incident illumination within the SWIR narrowband to the sensor. The filter can have first and second positions, the filter being optically coupled to the sensor in the first position, the filter being optically uncoupled to the sensor in the second position.

It is also contemplated that, in accordance with certain embodiments, the filter can include a first filter element and a second filter element. The first filter element can be arranged to communicate a first SWIR narrowband to the sensor and the second filter element can be arranged to communicate a second SWIR narrowband to the sensor. The first and second SWIR narrowbands can include peak absorption wavelengths that are different from one another. The first and second SWIR narrowbands can include peak reflectivity wavelengths that are different from one another. The first filter element can include a peak absorption wavelength and the second filter element can include a peak reflection wavelength.

In further embodiments the filter can include a third filter element and a fourth filter element. The third filter element can be arranged to communicate illumination in a third SWIR narrowband to the sensor and the fourth filter element can be arranged to communicate illumination in a fourth SWIR narrowband to the sensor. Alternatively the third and fourth filter elements can be arranged to communicate incident illumination to the sensor having different polarization than that communicated by the other filter element.

A method of detecting moisture in a solar cell includes selecting SWIR illumination within a narrowband including a peak absorption wavelength or a peak reflection wavelength of moisture to infrared illumination. The selected SWIR illumination is communicated to a solid-state sensor disposed within a camera, and image data indicating indication location of moisture within a solar cell array is generated. In certain embodiments an image can be displayed on a user interface showing the location of moisture within the solar cell array. Communicating the SWIR illumination can include illuminating the solar cell array with illumination constrained within the SWIR narrowband. Communicating the SWIR illumination can includes filtering illumination received from the solar cell array.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION OF THE PREFERRED EMBODIMENTS

Figure 1:
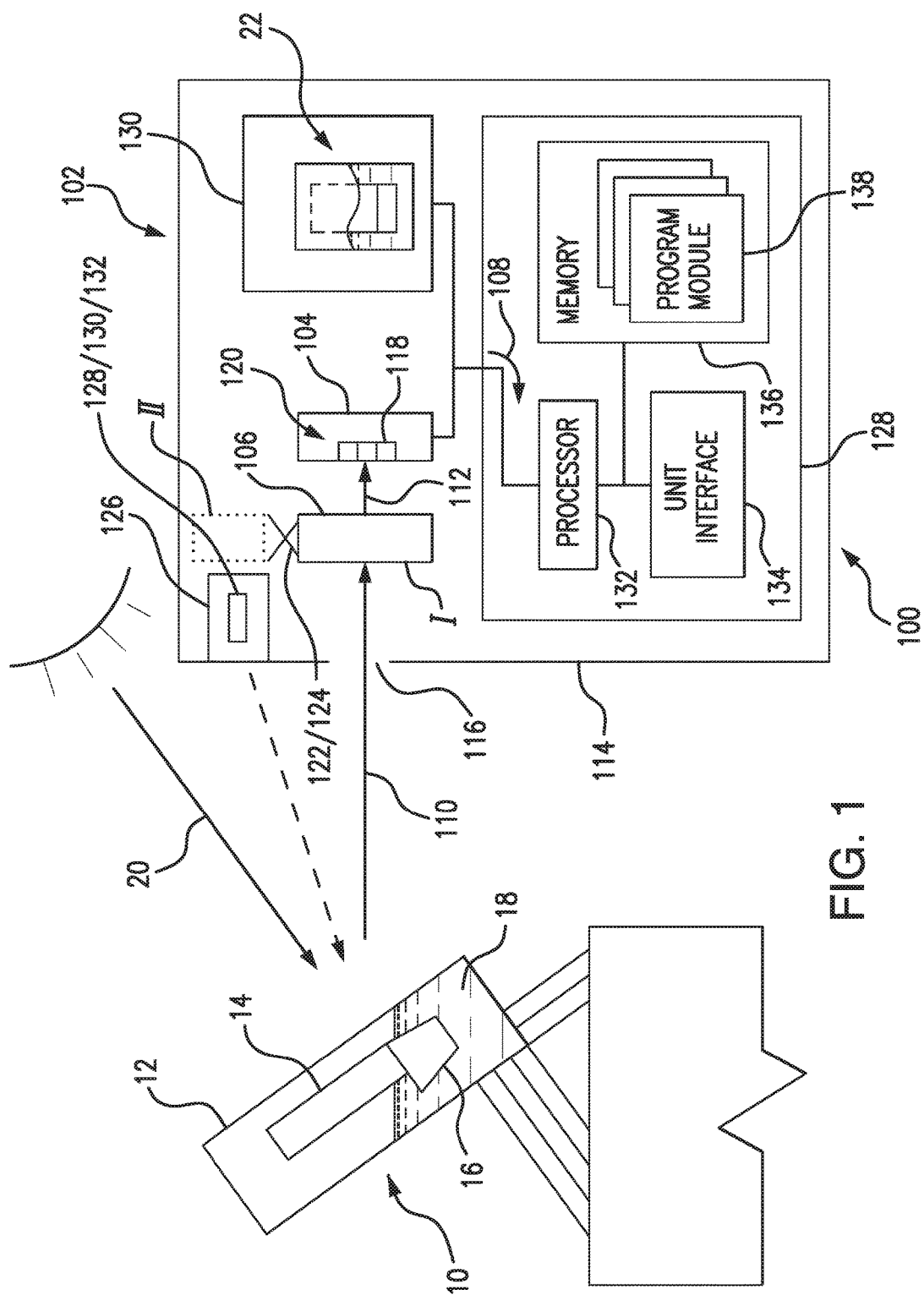
FIG. 1 is schematic view of the exemplary embodiment of an imaging apparatus for detecting moisture in a solar array, showing a short wavelength infrared (SWIR) imaging apparatus imaging a solar cell with light reflected from the solar cell.

Reference will now be made to the drawings wherein like reference numerals identify similar structural features or aspects of the subject disclosure. For purposes of explanation and illustration, and not limitation, a partial view of an exemplary embodiment of an imaging apparatus in accordance with the disclosure is shown in FIG. 1 and is designated generally by reference character 100. Other embodiments of imaging apparatuses and methods of detecting moisture using such apparatuses in accordance with the present disclosure, or aspects thereof, are provided in FIGS. 2-5, as will be described. The imaging apparatuses and associated methods of detecting moisture described herein can be used for detecting moisture in solar cells, such as in photovoltaic solar arrays, though the present disclosure is not limited to detecting moisture or to solar cells in general.

The human eye responds to light within the visible portion of the electromagnetic spectrum. Visible light is generally understood to have wavelengths between about 380 nanometers and about 720 nanometers. Electromagnetic radiation with wavelengths below 380 nanometers is generally described as ultraviolet radiation. Electromagnetic radiation with wavelengths above 720 nanometers is generally described as infrared radiation, inhabiting that portion of the electromagnetic spectrum.

The infrared portion of the electromagnetic spectrum is typically divided into the near-infrared (NIR) infrared spectrum portion, the short-wave infrared (SWIR) infrared spectrum portion, the mid-wave infrared (MWIR) infrared spectrum portion, and the long-wave (LWIR) infrared spectrum portion. As used herein, NIR refers to electromagnetic radiation with a wavelength between about 0.7 microns and about 1 micron. SWIR refers to electromagnetic radiation with a wavelength between about 1 micron and about 2.5 microns. MWIR refers to electromagnetic radiation with a wavelength between about 3 microns and 5 microns. LWIR refers to electromagnetic radiation with a wavelength between about between about 7 microns and 14 microns. As used herein, the term moisture includes water in a liquid state, water in a liquid state, water in a combination of liquid and vapor states, or water in a solid state (i.e. ice).

Referring to FIG. 1, imaging apparatus 100 is shown. Imaging apparatus 100 includes a camera 102 with a solid-state sensor 104. Solid-state sensor 104 is responsive to wideband SWIR illumination for generating image data 108 using illumination 110 collected from an object of interest within a field of view of camera 102. In the exemplary embodiments described herein the object of interest within the field of view of camera 102 is a solar cell 10. Solar cell 10 includes an enclosure 12 containing within its interior a photovoltaic element 14 and associated electronics (e.g., exposed conductors and circuitry) 16. Exemplary solar cell 10 also contains within its interior moisture 18 disposed within a lower (relative to gravity) portion of the enclosure, portions of photovoltaic element 14 and electronics 16 being bathed by moisture 18. A portion of moisture 18 is within the line of sight of camera 102; a portion of moisture is not within the line of sight of camera 18.

It is contemplated that imaging apparatus 100 can include a filter 106. Filter 106 enables use of broadband illumination, such as ambient illumination, e.g., solar light 20, reflected from solar cell 10. In this respect filter 106 is tuned to communicate illumination incident upon filter 106 to sensor 104 within a SWIR narrowband 112. Filter 106 is also tuned to attenuate (or block entirely) illumination of wavelengths outside of SWIR narrowband 112. SWIR narrowband 112 includes waveband featuring a peak absorption wavelength or peak reflection wavelength of water for infrared radiation, illumination communicated by filter 106 including information indicative of the presence of moisture 12 within solar cell 10. It is contemplated that SWIR narrowband 112 have a bandwidth that is between about 10 nanometers and about 100 nanometers. Bandwidths between about 10 nanometers and 100 nanometers allow SWIR narrowband to both feature a peak absorption wavelength or peak reflectivity wavelength, exclude the neighboring peak reflectivity wavelength (in the case of a SWIR narrowband feature a peak absorption wavelength), exclude the neighboring peak absorption wavelength (in the case of a SWIR narrowband featuring a peak reflectivity wavelength), and accommodate the dynamic response of sensors constructed using existing process equipment.

Camera 102 has a camera body 114 defining an aperture 116 and which houses sensor 104. Sensor 104 includes a plurality of indium gallium arsenide photodiodes 118. Photodiodes 118 are arranged in an array 120 for receiving a portion of illumination 110 reflected from solar cell 10 and entering camera body 114 through aperture 116. In embodiments employing filter 106, filter 106 is fixed along an axis 118 extending between aperture 116 and sensor 104, thereby being optically coupled to sensor 104.

In certain embodiments, filter 106 is movable relative to sensor 104. For example, filter 106 can have a first position I (shown in solid outline in FIG. 1) and a second position II (shown in dashed outline in FIG. 1). In first position I filter 106 is optically coupled to sensor 104 in first position I. In second position II filter 106 is optically uncoupled to sensor 104. This allows for acquiring image data of solar cell array using both narrowband illumination and broadband illumination, differences between images constructed from the image data sets providing indication of moisture within the imaged solar cell array. Filter 106 can be coupled to camera body 114 by, a flip mount 122 or a revolver structure 124, arranged to allow movement of filter 106 between first position I and second position II relative to sensor 104. Use of revolver also allows the use of narrowbands featuring different peak absorption wavelengths or peak reflectivity wavelengths, as will be described.

In accordance with certain embodiments, imaging device 100 can include an illuminator 126. Illuminator 126 can includes a narrowband illumination source, such as a laser source 128 or certain types of light-emitting-diode (LED) devices. Use of a narrowband source can eliminate the need to filter illumination reflected from the solar cell array 10. Illuminator 126 can include a broadband source, such as an incandescent source 130, a halogen source 132, or certain types of broadband LED devices. Such sources can provide illumination under difficult or adverse conditions, such as when there are competing sources of illumination in the ambient environment.

Imaging apparatus 100 also includes a control module 128. Control module 128 is communicative with sensor 104 and a display 130, and is configured and adapted to construct an image 22 using image data 108 for display on display 130. It is contemplated that image 22 include information relating to the presence of moisture within solar cell 10, region having moisture 18 having enhanced or reduced detail for example. Control module 128 can be implemented by either or both of software and circuitry, exemplary control module 128 having a processor 132 disposed in communication with a user interface 134 and a memory 136. Memory 136 has recorded thereon a plurality of program modules 138 which, when read by processor 132, cause processor to undertake certain actions, including those of the methods of detecting moisture detailed below.

Figure 2:
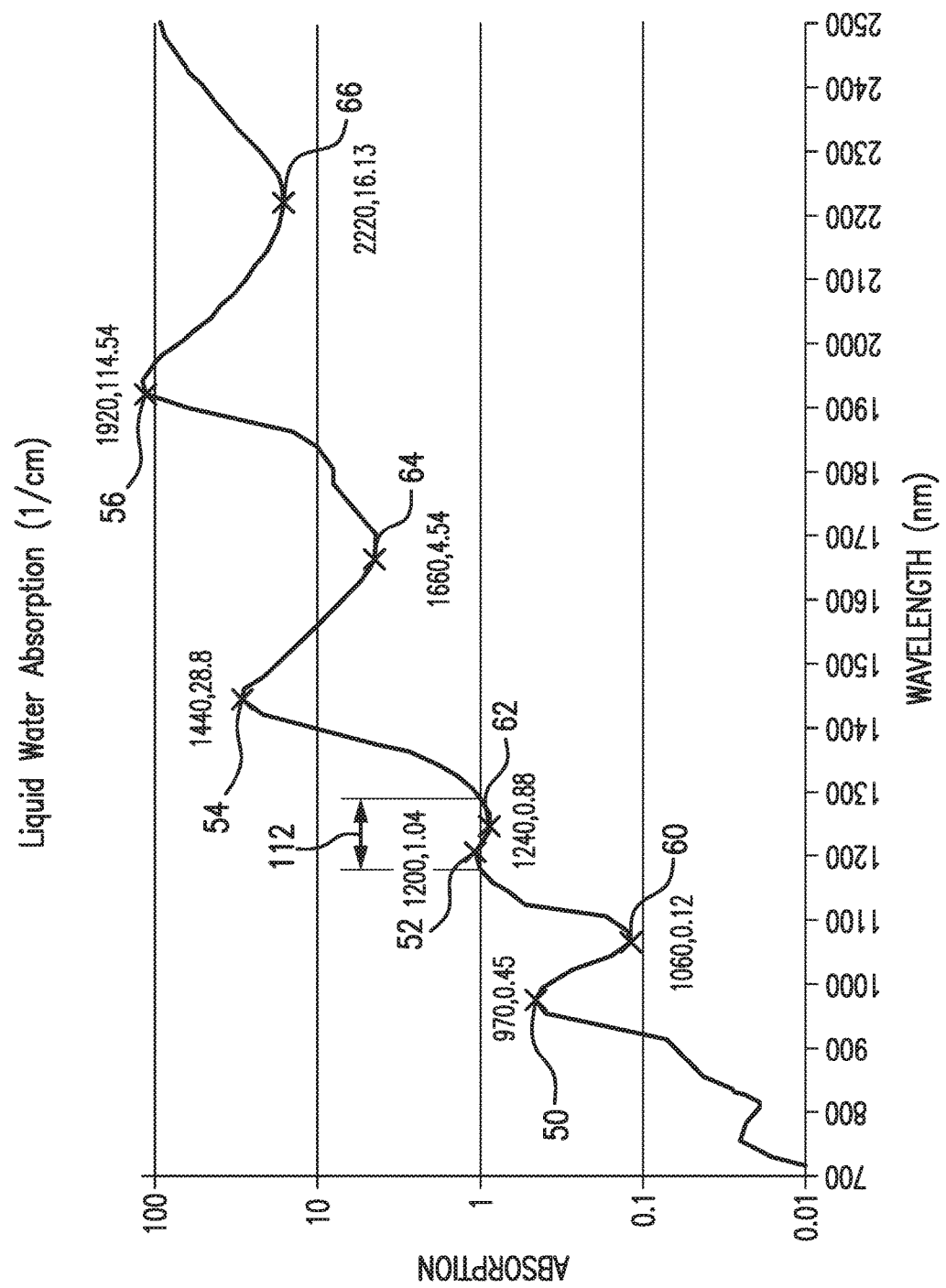
FIG. 2 is chart of absorptivity of water to electromagnetic radiation, showing relative peak absorption and peak reflection wavelengths of water within the SWIR waveband.

Referring to FIG. 2, a graph of absorptivity and reflectivity of water as a function of wavelength are shown. Absorptivity is indicated logarithmically on the y-axis. Wavelength is shown on the y-axis. Absorption peaks for water to infrared radiation are indicated with reference numerals 50-56. Reflection peaks for water to infrared radiation are indicated with reference numerals 60-66. An exemplary SWIR narrowband 112 is shown featuring a peak absorption wavelength 52.

In certain embodiments, SWIR narrowband 112 can include at least one peak absorption wavelength. For example, SWIR narrowband 112 can include a first peak absorption wavelength 50 that occurs at about 0.97 microns. SWIR narrowband 112 can include a second peak absorption wavelength 52 that occurs at about 1.2 microns. SWIR narrowband 112 can include a third peak absorption wavelength 54 that occurs at about 1.44 microns. SWIR narrowband 112 can include a fourth peak absorption wavelength 56 that occurs at about 1.92 microns.

Peak absorption wavelengths 50-56 result from infrared radiation causing the moisture molecule to vibrate at harmonic frequencies relative to the fundamental vibration frequencies of the moisture molecule, which in turn cause absorbance at 2.898, 2.766 and 6.097 microns, which are outside the SWIR range. Detecting these absorbance bands is generally relatively difficult due to expensive imaging detectors and wavelength emission due to the temperature of the objects and the imaging components themselves. However, since SWIR illumination reflected from solar cell 10 at (and around) peak absorption wavelengths exhibits reduced intensity in portions of solar cell 10 having moisture relative to portions of solar cell 10 without moisture, image data collected using such wavelengths provides information relating to the presence of moisture in the solar cell array, portions of the solar cell array having moisture reflecting less illumination in the SWIR narrowband than portions of the solar cell array not having moisture, thereby showing less detail in an image.

One advantage on using illumination within SWIR narrowband 112 is that solar cell array 10 can be imaged without use of the peak absorptivity wavelengths for the moisture molecule in the MWIR band. Since transparent elements commonly protect the solar cells from the external environment, typically with a glass or plastic structure, MWIR and LWIR cameras generally cannot see beneath the surface of the cell. Therefore, MWIR and LWIR imaging cameras typically are unable to detect moisture absorption occurring under the glass. MWIR and LWIR cameras are thus generally limited to image solar cells to detect thermal disturbances as evidence of problems, such as electrical problems that result subsequent to moisture infiltration or evaporative cooling of moisture might show up as a cooler portion of a panel. In contrast, embodiments of the imaging apparatus described herein provide moisture detection prior to the moisture inducing electrical problems.

In accordance with certain embodiments, SWIR narrowband 112 can include at least one peak reflection wavelength. For example, SWIR narrowband 112 can include a first peak reflection wavelength 60 that occurs at about 1.06 microns. SWIR narrowband 112 can include a second peak reflection wavelength 62 that occurs at about 1.24 microns. SWIR narrowband 112 can include a third peak reflection wavelength 64 that occurs at about 1.66 microns. SWIR narrowband 112 can include a fourth peak reflection wavelength 66 that occurs at about 2.22 microns.

Peak reflection wavelengths 60-66 are wavelengths in the SWIR waveband where moisture reflects relatively larger amounts of incident infrared electromagnetic radiation due to an absence of absorption of energy from incident illumination by moisture molecules. This causes SWIR narrowband illumination reflected from solar cell 10 to exhibit increased intensity in portions of solar cell array 10 not having moisture relative to portions of solar cell array 10 having moisture, image data collected using such wavelengths providing information relating to the portions of solar cell 10 without moisture.

Figure 3:
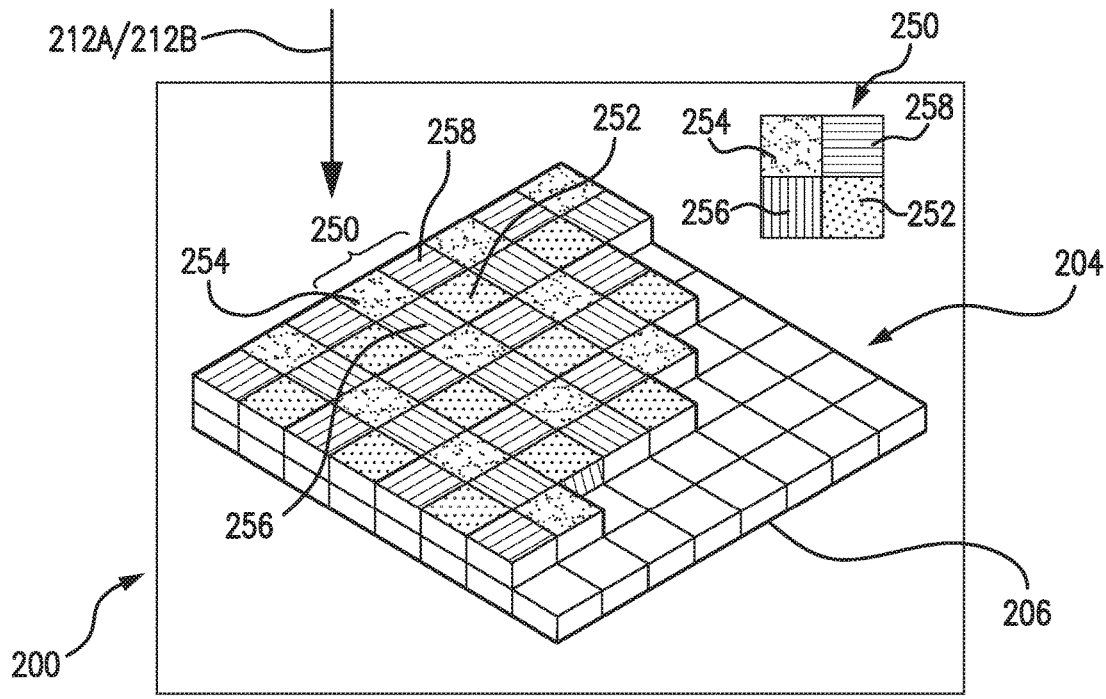
FIG. 3 is a schematic view of a another embodiment of an imaging apparatus, showing an imaging device having a patterned filter.

With reference to FIG. 3, an imaging apparatus 200 is shown. Imaging apparatus 200 is similar to imaging apparatus 100 and additionally includes a filter 204. Filter 204, which may be a Bayer-type filter, is fixed relative to sensor 206 and a plurality of filter elements. Filter 204 has filter elements arranged in a quad pattern 250. Quad pattern 250 includes a first filter element 252, a second filter element 254, a third filter element 256, and a fourth filter element 258. Each of the filter elements 252-258 are optically coupled to sensor 206 and adjacent to one another such that a single corner of any of the four filter elements is adjacent to a corner of the other three filter elements in the quad pattern.

First filter element 252 is arranged to communicate a first SWIR narrowband 212A and second filter element 254 is arranged to communicate a second SWIR narrowband 212B. Second SWIR narrowband 212B is different than first SWIR narrowband 212A. For example, first SWIR narrowband 212A and second SWIR narrowband 212B can include a SWIR narrowband featuring different peak absorption wavelengths, e.g., peak absorptivity wavelengths 50-56 (shown in FIG. 2). In certain embodiments, first SWIR narrowband 212A and second SWIR narrowband 212B can each feature different peak reflection wavelengths, e.g., relative peak reflectivity wavelength 60-66 (shown in FIG. 2). In accordance with certain embodiments, one of first SWIR narrowband 212A and second SWIR narrowband 212B can include a peak absorption wavelength and the other of first SWIR narrowband 212A and second SWIR narrowband 212B can include a peak reflection wavelength.

Third filter element 256 is arranged to communicate incident illumination with a polarization that is 90 degrees from that communicated by fourth filter element 258. For example, third filter element 256 can communicate incident illumination with 90-degree polarization and fourth filter element 258 can communicate incident illumination with 0-degree polarization. Alternatively, third filter element 256 can communicate incident illumination with 45-degree polarization and fourth filter element 258 can communicate incident illumination with 135-degree polarization. Inclusion of filter elements that communicate incident illumination with different polarization adjacent to filter elements communicating incident illumination within SWIR narrowbands can provide additional information, for example corroboration of moisture presence, such as detecting stress in various layers of material in the field of view of the imaging apparatus, which can indicate ice formation within an imaged solar cell array.

Figure 4:
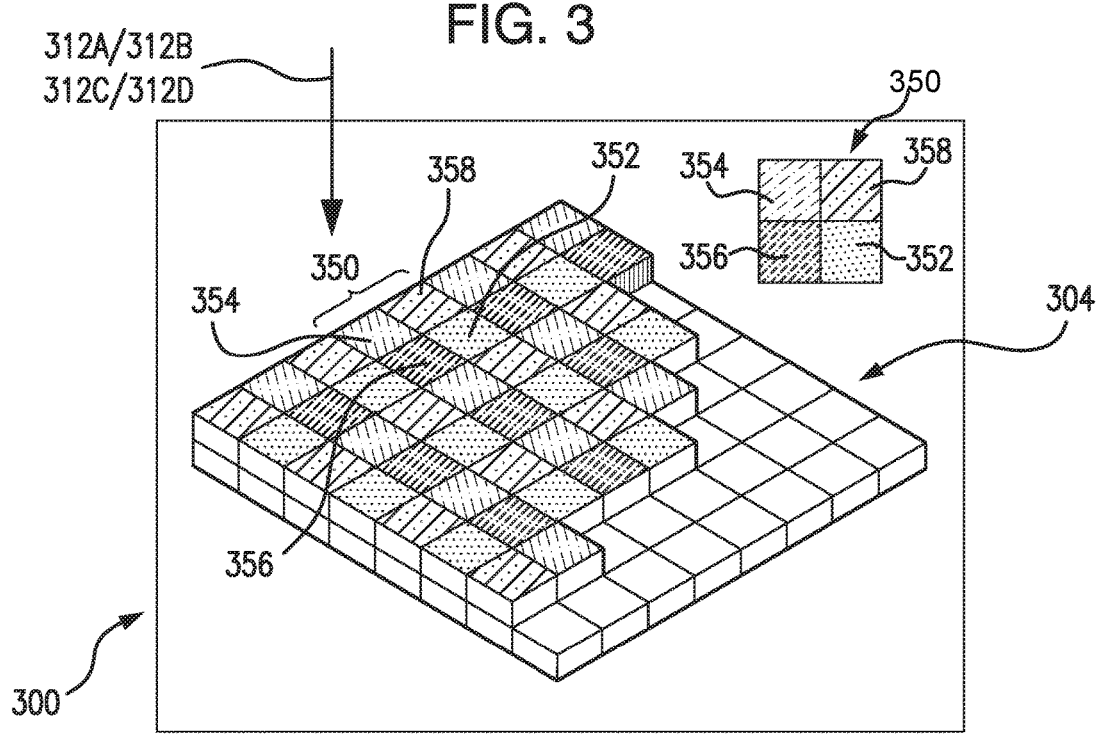
FIG. 4 is a schematic of a yet another embodiment of an imaging apparatus, showing an imaging device having another patterned filter.

With reference to FIG. 4, an imaging apparatus 300 is shown. Imaging apparatus 300 is similar to imaging apparatus 200 and additionally includes a filter 304. Filter 304 is similar to filter 204 and includes a quad pattern 350 of filter elements. Each of the filter elements includes is arranged to communicate one of four SWIR narrowbands. Quad pattern 350 includes a first filter element 352 arranged to communicate a first SWIR narrowband 312A, a second filter element 354 arranged to communicate a second SWIR narrowband 312B, a third filter element 356 arranged to communicate a third SWIR narrowband 312C, and fourth filter element 358 arranged to communicate a fourth SWIR narrowband 312D. As moisture is $H_2O$ and its absorbance are associated with the O—H bonds in water, use of four filter elements configured to communicate four SWIR narrowbands features different peak absorption/reflection wavelengths enables detection in the presence of other interferences, such as C—H, N—H or C—O bonds in the plastics or gases present in air. Mirror-like reflections can also be present in some solar cell arrays, which result in high intensity in all wavebands. Sensing such reflection or other interferences, the imager processor could ignore such regions of the image.

Figure 5:
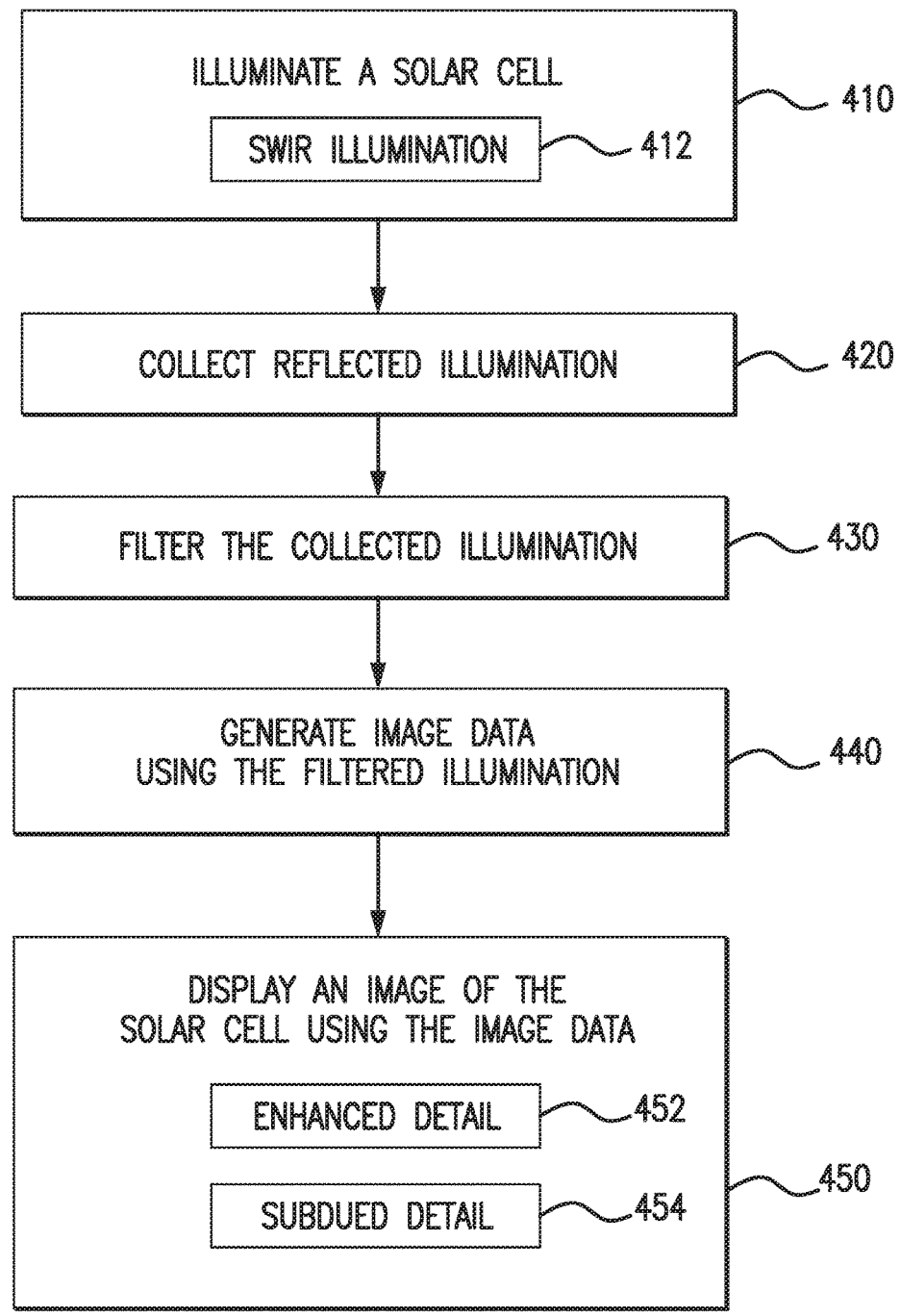
FIG. 5 is a process flow diagram of a method of detecting moisture infiltration in a solar cell using an imaging device, showing steps of the method.

With reference to FIG. 5, a method 400 of detecting moisture in a solar cell array, e.g., solar cell array 10 (shown in FIG. 1), is shown. Method 400 includes illuminating the solar cell array with illumination, e.g., solar light 20 (shown in FIG. 1), as shown with box 410. The illumination includes electromagnetic radiation within a SWIR waveband, e.g., SWIR narrowband 112 (shown in FIG. 1), as shown with box 412.

A portion of the illumination is reflected by the solar cell and collected by an imaging apparatus, e.g., imaging apparatus 100 (shown in FIG. 1), as shown with box 420. It is also contemplated that the illumination received by the imaging device can include broadband illumination such as from a halogen-based light source, e.g., from halogen source 128 (shown in FIG. 1), or from an LED source, e.g., from LED source 130 (shown in FIG. 1). In accordance with certain embodiments, the illumination recited received by the imaging apparatus can include narrow band illumination, e.g., from fixed or tunable wavelength laser source 132 (shown in FIG. 1).

The imaging device filters the received illumination reflected from the solar cell, as shown with box 430. Filtering the illumination can include filtering the reflected illumination by excluding wavelengths outside of SWIR narrowband, e.g., outside of SWIR narrowband 112 (shown in FIG. 2). Filtering can include moving a filter, e.g., filter 106 (shown in FIG. 1), from an optically coupled position to an optically uncoupled position, e.g., from uncoupled position II (shown in FIG. 1) to coupled position I (shown in FIG. 1). Filtering can include communicating a plurality of SWIR narrowbands to the sensor, e.g., with filter 204 (shown in FIG. 3) or with filter 304 (shown in FIG. 4). Filtering can include communicating illumination having more than one polarization, such as with filter 304 (shown in FIG. 4), the imaging apparatus sensor for purposes of detecting strain in silicon or glass, which can corroborate the presence of moisture with damage associated with the freeze and thaw cycle within an imaged solar cell. As will be appreciated, filtering also includes attenuating (or removing entirely) intensity of illumination outside the SWIR narrowband of the filter.

The sensor generates image data, e.g., image data 108 (shown in FIG. 1), using the received SWIR narrowband illumination, as shown with box 440. An image is then generated using the image data based on intensity of wavelengths within the SWIR narrowband and output to a display, as shown with box 450. It is contemplated that the image provide enhanced or subdued amounts of detail in portions of the solar cell, including portions where moisture may out of the line of sight of the imaging apparatus, owing to the ability of SWIR illumination to penetrate some types of silicon structures. In this respect detail can be removed from the image in image portions without moisture, thereby making more clear regions of the solar cell array where moisture is not present, as shown with box 452. The method can also include enhancing detail in image portions with moisture, thereby making more clear regions of the solar cell array where moisture is present, as shown with box 454.

The methods and systems of the present disclosure, as described above and shown in the drawings provide for moisture detection apparatus and methods with superior properties including the ability to detect moisture within solar cell enclosures. In certain embodiments, moisture can be detected non-invasively and rapidly by imaging an array of solar cells with a hand-held device, such as camera. In accordance with certain embodiments, moisture can be detected in large arrays, e.g., a solar farm, or a remote location, e.g., a rooftop installation, by flying a UAV equipped with a camera over one or more of the solar cells and acquiring image data of the solar cells. Further, moisture can be detected in the presence of interferences, such as from vibration of molecular bonds in plastics and airborne contaminants. While the apparatus and methods of the subject disclosure have been shown and described with reference to preferred embodiments, those skilled in the art will readily appreciate that change and/or modifications may be made thereto without departing from the scope of the subject disclosure.

What is claimed is:

1. An imaging apparatus, comprising:
a camera having a solid-state sensor; and
an illumination selector arranged for optical coupling with the sensor, wherein the selector is operative to communicate electromagnetic radiation in a predetermined waveband to the sensor, the predetermined waveband including a peak absorption or a peak reflection wavelength of moisture to infrared illumination for imaging moisture disposed within a solar cell array, wherein the selector includes a filter arranged to communicate incident illumination within the waveband to the sensor, wherein the filter comprises a first filter element and a second filter element, the first filter element being arranged to communicate incident illumination within a first SWIR narrowband to the sensor, and wherein the second filter element is arranged to communicate incident illumination within a second SWIR narrowband to the sensor, wherein the first SWIR narrowband includes a peak absorption wavelength, wherein the second SWIR narrowband includes a peak reflection wavelength.

2. The apparatus as recited in claim 1, wherein the sensor is responsive to illumination within a waveband between about 0.8 microns and about 2.6 microns.

3. The apparatus as recited in claim 1, wherein the sensor includes an array of indium-gallium-arsenide photodiodes.

4. The apparatus as recited in claim 1, wherein the waveband includes a peak absorption wavelength selected from a group including 0.97, 1.2, 1.44, and 1.92 microns.

5. The apparatus as recited in claim 1, wherein the waveband includes a peak reflection wavelength selected from a group including 1.06, 1.24, 1.66, and 2.22 microns.

6. The apparatus as recited in claim 1, wherein the waveband is a shortwave infrared waveband with a bandwidth between about 10 nanometers and about 100 nanometers.

7. The apparatus as recited in claim 1, wherein the selector includes light source constrained to emit electromagnetic radiation within the waveband.

8. The apparatus as recited in claim 7, wherein the light source includes an incandescent, halogen, light-emitting-diode, or laser illuminator.

9. The apparatus as recited in claim 1, wherein the filter has a first position, wherein the filter is optically coupled to the sensor, and a second position, wherein the filter is optically uncoupled from the sensor.

10. The apparatus as recited in claim 1, wherein the first SWIR narrowband includes a peak absorption wavelength that is different than a peak absorption wavelength included within the second SWIR narrowband.

11. The apparatus as recited in claim 1, wherein the first SWIR narrowband includes a peak reflection wavelength that is different than a peak reflection wavelength included within the second SWIR narrowband.

12. The apparatus as recited in claim 1, wherein the filter includes a third filter element and a fourth filter element, wherein the third filter element is arranged to communicate incident illumination in a third SWIR narrowband to the sensor, wherein the fourth filter element is arranged to communicate incident illumination in a fourth SWIR narrowband to the sensor.

13. The apparatus as recited in claim 1, wherein the filter includes a third filter element and a fourth filter element, wherein the fourth filter element is arranged to communicate incident illumination with a polarization that is different than polarization of incident illumination communicated by the third filter element.

14. A method of detecting moisture in a solar cell, comprising:
sensing electromagnetic radiation reflected from a solar cell array;
analyzing the sensed electromagnetic radiation in one or more predetermined waveband wherein water molecules have strong absorption/or strong reflection; and
identifying locations within the solar cell array that have a high likelihood that water is present at locations where the selected wavebands sensed are lower than portions of the solar cell surrounding the locations for highly absorbed selected wavelengths and are higher than portions of the solar cell array surrounding locations for high reflected wavelengths, wherein sensing includes using a selector wherein the selector includes a filter arranged to communicate incident illumination within the predetermined waveband to a sensor, wherein the filter comprises a first filter element and a second filter element, the first filter element being arranged to communicate incident illumination within a first SWIR narrowband to the sensor, and wherein the second filter element is arranged to communicate incident illumination within a second SWIR narrowband to the sensor, wherein the first SWIR narrowband includes a peak absorption wavelength, wherein the second SWIR narrowband includes a peak reflection wavelength.

15. The method as recited in claim 14, further comprising generating an image on a user interface showing moisture disposed within the solar cell array.

* * * * *